(12) United States Patent
Schmaus et al.

(10) Patent No.: US 12,053,537 B2
(45) Date of Patent: Aug. 6, 2024

(54) REDUCTION OF STINGING SENSATION ON SKIN

(71) Applicant: Symrise AG, Holzminden (DE)

(72) Inventors: Gerhard Schmaus, Höxter (DE); Sabine Lange, Holzminden (DE); Eric Gruber, Holzminden (DE)

(73) Assignee: Symrise AG, Holzminden (DE)

( * ) Notice: Subject to any disclaimer, the term of this patent is extended or adjusted under 35 U.S.C. 154(b) by 688 days.

(21) Appl. No.: 15/773,767

(22) PCT Filed: Nov. 15, 2015

(86) PCT No.: PCT/EP2015/076634
§ 371 (c)(1),
(2) Date: May 4, 2018

(87) PCT Pub. No.: WO2017/080625
PCT Pub. Date: May 18, 2017

(65) Prior Publication Data
US 2019/0060193 A1    Feb. 28, 2019

(51) Int. Cl.
| | | |
|---|---|---|
| *A61K 8/34* | (2006.01) |
| *A61K 8/02* | (2006.01) |
| *A61K 8/04* | (2006.01) |
| *A61K 8/60* | (2006.01) |
| *A61K 8/73* | (2006.01) |
| *A61K 8/92* | (2006.01) |
| *A61K 9/00* | (2006.01) |
| *A61K 9/06* | (2006.01) |
| *A61K 9/107* | (2006.01) |
| *A61K 9/16* | (2006.01) |
| *A61K 31/047* | (2006.01) |
| *A61K 47/02* | (2006.01) |
| *A61K 47/08* | (2006.01) |
| *A61K 47/10* | (2017.01) |
| *A61K 47/12* | (2006.01) |
| *A61K 47/14* | (2017.01) |
| *A61K 47/18* | (2017.01) |
| *A61K 47/22* | (2006.01) |
| *A61K 47/26* | (2006.01) |
| *A61K 47/32* | (2006.01) |
| *A61K 47/34* | (2017.01) |
| *A61K 47/36* | (2006.01) |
| *A61Q 19/00* | (2006.01) |
| *A61Q 19/02* | (2006.01) |

(52) U.S. Cl.
CPC .............. *A61K 8/347* (2013.01); *A61K 8/022* (2013.01); *A61K 8/046* (2013.01); *A61K 8/60* (2013.01); *A61K 8/732* (2013.01); *A61K 8/922* (2013.01); *A61K 9/0014* (2013.01); *A61K 9/06* (2013.01); *A61K 9/107* (2013.01); *A61K 9/1617* (2013.01); *A61K 9/1623* (2013.01); *A61K 9/1652* (2013.01); *A61K 9/1658* (2013.01); *A61K 31/047* (2013.01); *A61K 47/02* (2013.01); *A61K 47/08* (2013.01); *A61K 47/10* (2013.01); *A61K 47/12* (2013.01); *A61K 47/14* (2013.01); *A61K 47/18* (2013.01); *A61K 47/22* (2013.01); *A61K 47/26* (2013.01); *A61K 47/32* (2013.01); *A61K 47/34* (2013.01); *A61K 47/36* (2013.01); *A61Q 19/00* (2013.01); *A61Q 19/005* (2013.01); *A61K 2800/10* (2013.01); *A61K 2800/31* (2013.01); *A61K 2800/56* (2013.01); *A61K 2800/75* (2013.01); *A61Q 19/02* (2013.01)

(58) Field of Classification Search
CPC ...... A61K 8/347; A61K 9/0014; A61K 47/14; A61K 47/36; A61Q 19/005; A61Q 19/00; A61Q 19/02
See application file for complete search history.

(56) References Cited

U.S. PATENT DOCUMENTS

| | | | | |
|---|---|---|---|---|
| 2007/0098655 A1* | 5/2007 | Schmaus | ................ | A61K 8/347 424/62 |
| 2008/0311209 A1* | 12/2008 | Beumer | ................ | A61Q 19/08 424/59 |
| 2011/0171288 A1* | 7/2011 | Mohammadi | .......... | A61Q 19/02 424/450 |
| 2013/0028976 A1* | 1/2013 | Gregson | ................ | A23P 10/30 424/490 |
| 2014/0079747 A1 | 3/2014 | Dihora et al. | | |

FOREIGN PATENT DOCUMENTS

| | | |
|---|---|---|
| WO | 2006/082536 A1 | 8/2006 |
| WO | 2009/105294 A2 | 8/2009 |
| WO | 2011/121515 A1 | 10/2011 |

OTHER PUBLICATIONS

"Phenethyl resorcinol," The Good Scent Company, <http://www.thegoodscentscompany.com/data/rw1117221.html>, published Mar. 16, 2013, p. 1-2.*
K. Inoue et al., "Evaluation of Stinging-inducing Chemicals using Cultured Neuronal Cells: an Electrophysiological Approach," Toxicology in Vitro 10 (1996) 455-462.*
H. Fan et al., "Development of a nanostructured lipid carrier formulation for increasing photo-stability and water solubility of Phenylethyl Resorcinol," Applied Surface Science 288, Available Online Oct. 12, 2013, pp. 193-200.*
S.S. Bansode et al., "Microencapsulation: A Review," International Journal of Pharmaceutical Sciences Review and Research, vol. 1, Issue 2, Mar.-Apr. 2010; Article 008, pp. 38-43.*

(Continued)

*Primary Examiner* — Monica A Shin
(74) *Attorney, Agent, or Firm* — Dilworth & Barrese, LLP

(57) ABSTRACT

The present invention belongs to the area of cosmetics that comprise at least an active agent which cause stinging, pricking, tingling and burning sensation on skin as a side effect. The invention in particular relates to a spray dried composition and the method as well as the use of the spray dried composition comprising said stinging, pricking, tingling and burning active agents to reduce and/or inhibit stinging, pricking, tingling and burning sensation on skin.

4 Claims, No Drawings

(56) References Cited

OTHER PUBLICATIONS

A. Parikh et al., "A Review on Applications of Maltodextrin in Pharmaceutical Industry," International Journal of Pharmacy and Biological Sciences, vol. 4, Issue 4, Oct.-Dec. 2014, pp. 67-74.*
M. I. Ré, "Microencapsulation by Spray Drying," Drying Technology, 16(6), 1195-1236 (1998).*
Mintel, "Henna Hair Colours Colouring Powder," Jan. 2015; Database accession No. 2910353; Database GNPD.
Hansen et al., "Process characteristics and compaction of spray-dried emulsions containing a drug dissolved in lipid," International Journal of Pharmaceutics, Elsevier, 287(1-2): 2004, pp. 55-66.

* cited by examiner

REDUCTION OF STINGING SENSATION ON SKIN

FIELD OF INVENTION

The present invention belongs to the area of cosmetics that comprise at least an active agent which causes stinging, pricking, tingling and burning sensation on skin as a side effect. The invention in particular relates to a spray dried composition and the method as well as the use of the spray dried composition comprising said stinging, pricking, tingling and burning active agents to reduce and/or inhibit stinging, pricking, tingling and burning sensation on skin.

STATE OF THE ART

In a large number of cases, topical products contain actives which may produce a feel of discomfort and stinging sensation when applied to the skin. Especially people with extremely sensitive skin or skin areas (e.g. face) prone to feel this kind of sensation. The present invention is directed in part to compositions and methods for inhibiting or reducing the stinging sensation associated with such topical products. The occurrence, frequency and nature of topical-product-induced stinging often varies from user to user. The severity of discomfort to the susceptible user may range from subclinical to mild. Typical symptoms of this feeling of discomfort are itching (pruritus), stinging, burning and tingling.

Many chemical substances are able to produce stinging when topically applied to the skin. Many actives used in topical products are known to be slightly stinging, especially to people with "sensitive skin". These ingredients include fragrances, preservatives, solvents, propellants and many other ingredients that might otherwise be considered inert components of the products. Additionally, many topical product active ingredients, including chemicals that may also be classified as drugs, produce irritation when applied to the skin. These include, but are not limited to, such ingredients as skin cell renewal agents, anti-ageing agents, anti-acne drugs, antiperspirant compounds, antihistamines, anti-inflammatory agents, skin protective agents, insect repellent chemicals, sunscreens, whitening agents and many others. The vehicles in which the active ingredients are formulated may also produce irritation in sensitive people.

Therefore the need exists for a composition and method for cosmetics that reduces or inhibits the feeling of stinging, pricking or tingling discomfort.

Accordingly, an object of the present invention was to provide a method or a stable composition, which comprises at least one kind of slightly stinging, pricking, tingling and burning active agent, which, when applied to the skin is less stinging. In particular, an object of the invention was to provide a composition containing at least one kind of active agent when formulated into cosmetic or pharmaceutical preparations shows reduction/decrease of stinging and pricking on the skin. A further object was, in particular, to formulate a stable preparation with the developed composition containing at least one kind of stinging, pricking, tingling and burning active agent, such as skin whitening preparations, leave-on hair products and hair colorations, and simultaneously keep the function capability of the active agent with optimal efficacy. Further object was to improve the feeling of the skin through the reduction/decrease of stinging and pricking caused by the composition containing the at least one kind of stinging, pricking, tingling and burning active agent.

DESCRIPTION OF THE INVENTION

Subject of the present invention is a spray dried composition comprising
(i) one or more active agents which causes discomfort feelings like stinging, pricking, tingling and burning sensation when applied onto skin,
(ii) one or more carrier materials which are selected from the group consisting of sugar, sugar derivatives, modified starch, triglycerides, fatty alcohols or esters of fatty alcohols and fatty acids, proteins, celluloses, salts, dextrins, gums, sugar alcohols, polyols, peptides, acids, carbohydrates or hydrocolloids.

Surprisingly, it has been observed that there is less feeling of stinging, pricking, tingling and burning on the skin, when the active agents which should be formulated in cosmetic preparations are spray dried using the said carrier materials before the agents are provided into the cosmetic preparations.

When using more than one stinging, pricking, tingling and burning active agent, each active agent is preferably provided spray dried individually or in case that the agents are compatible with each other they could also be spray dried together to obtain one single kind of spray dried composition.

The stinging, pricking, tingling and burning active agents of the present invention are preferably compounds which may each on their own possess different functions in a cosmetic preparation, e.g. an active agent in the sense of the invention may be selected from whitening or brightening agents, skin cell renewal agents, anti-ageing agents, antimicrobials, anti-acne drugs, antiperspirant compounds, antihistamines, anti-inflammatory agents, skin protective agents, insect repellent chemicals, sunscreens, fragrances, preservatives, actives for hair coloration, solvents, propellants.

The whitening or brightening agent in the sense of the present invention is preferably selected from skin whitening agent or hair brightening agent (bleaching products), most preferably the whitening or brightening agent of the present invention is a skin whitening agent. Preferably the whitening agent is 4-(1-Phenylethyl) 1-,3 benzenediol.

Especially preferred stinging, pricking, tingling and burning active agents are compounds which are derivatives from an alcohol. Preferably the alcohol derivatives are selected from the group consisting of phenol derivatives; in particular the active agents are preferably not carboxylic acid derivatives.

In a preferred embodiment the stinging, pricking, tingling and burning active agents are alcohol derivatives, which are phenol derivatives, that are hydroxybenzol derivatives which preferably comprises one, two or three hydroxyl groups as residues which are attached to the ring skeleton. Preferably the stinging, pricking, tingling and burning active agents are alcohol derivatives which are resorcinol derivatives, such as formula (I)

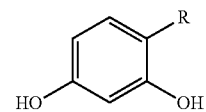

wherein R stands for an alkyl radical having 3 to 10 carbon atoms or an optionally substituted alkylphenyl radical having 8 to 16 carbon atoms.

Preferably the stinging, pricking, tingling and burning active agents which are resorcinol derivatives are selected from the group consisting of butyl resorcinol, pentyl resorcinol, hexyl resorcinol, heptyl resorcinol, octyl resorcinol, nonyl resorcinol, decylresorcinol, phenylethyl resorcinol, phenylpropyl resorcinol, phenylbutyl resorcinol, phenylhexyl resorcinol, toluoylethyl resorcinol, toluoylpropyl resorcinol, toluoylbutyl resorcinol, toluoylhexyl resorcinol, methoxytoluoylethyl resorcinol, methoxytoluoylpropyl resorcinol, methoxytoluoylbutyl resorcinol, methoxytoluoylhexyl resorcinol, dimethoxytoluoylethyl resorcinol, dimethoxytoluoylpropyl resorcinol, dimethoxytoluoylbutyl resorcinol, dimethoxytoluoylhexyl resorcinol and mixtures thereof.

The combination of the described active agents with certain kind of carrier materials as defined herein shows the advantage of reduced and decreased stinging, pricking, tingling and burning on the skin.

Suggested ranges of described active agents in a spray dried composition (which is not the end product) are from 0.001 to 60% b.w., preferably from 0.01 to 50% b.w., more preferably from about 0.1 to 40% b.w. of the total spray dried composition.

Suitable carrier materials are selected from sugars such as sucrose, glucose, lactose, levulose, trehalose, fructose, maltose, ribose, dextrose, isomalt, sorbitol, mannitol, xylitol, lactitol, maltitol, pentatol, arabinose, pentose, xylose, galactose; hydrogenated starch hydrolysates, inulin, and oligosaccharides such as oligofructose; maltodextrins or dextrins (soluble fiber); hydrocolloids such as agar, gum acacia, modified gum acacia, sodium alginate, potassium alginate, ammonium alginate, calcium alginate or carrageenan; gums; polydextrose; celluloses such as sodium carboxymethylcellulose, enzymatically hydrolyzed carboxy methyl cellulose, methyl cellulose, hydroxypropyl cellulose and hydroxypropyl methyl cellulose; triglycerides such as medium-chain triglycerides (MCT) whose fatty acids have an aliphatic tail of 6-12 carbon atoms, and long-chain triglycerides (LCT) whose fatty acids have an aliphatic tail of 14-24 carbon atoms; proteins such as gelatin, milk protein, pea protein, soy and whey protein and whey protein isolates and hydrolysates, and sodium caseinates; Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular dioctyl malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes and derivatives and mixtures thereof.

Preferably the carrier material is a mixture of maltodextrin, caprylic/capric triglyceride and a modified starch.

The modified starch is preferably based on potato starch, wheat starch, rice starch and corn starch, and mixture thereof.

Suggested ranges of carrier materials in a spray dried composition (which is not the end product) are from 10 to 90% b.w., preferably from 10 to 80% b.w., more preferably from about 20 to 70% b.w. of the total spray dried composition.

A further aspect of the invention is a spray dried composition comprising
(a) one or more stinging pricking, tingling and burning active agents from 0.001 to 60% by weight,
(b) one or more carrier material from 10 to 90% by weight,
(c) one or more further additives from 0 to 20% by weight.

The active agents and carrier materials are as defined herein.

Suitable further additives may be selected from solvents, cosmetically acceptable carriers, and further active agents.

In a preferred embodiment of the spray dried composition of the present invention the carrier material is selected from oligosaccharides, modified starches, medium chain triglycerides (MCT) or a mixture thereof.

In a preferred embodiment of the spray dried composition of the present invention the carrier material is maltodextrin and/or caprylic/capric triglyceride.

In a further preferred embodiment of the spray dried composition of the present invention the carrier is a mixture of maltodextrin and caprylic/capric triglyceride and/or modified starch.

In a preferred embodiment of the invention a spray dried composition comprises at least an active agent which is preferably phenylethyl resorcinol.

Especially the combination of phenylethyl resorcinol and carrier materials which is a mixture comprising maltodextrin, caprylic/capric triglycerides and a modified starch, which is preferably sodium starch octenylsuccinate has shown that the stinging, pricking, tingling and burning of the skin when applying the cosmetic product comprising said spray drying composition onto skin could be decreased through the impact of the spray dried composition.

Another aspect of the present invention is a method of reducing and/or inhibiting stinging, pricking, tingling and burning sensation of a cosmetic by comprising the step of spray drying the one or more active agents which are comprised in the cosmetic preparation by using one or more carrier materials which are selected from sugar, sugar derivatives, modified starch, triglycerides, proteins, celluloses, salts, dextrins, gums, sugar alcohols, polyols, peptides, acids, carbohydrates or hydrocolloids, before formulating said active agents into the cosmetic preparation.

The method of the present invention thus reduce and/or inhibit skin stinging, pricking, tingling and burning caused by the topical application of a cosmetic preparation containing the active agents which are preferably derivatives from an alcohol, particularly alcohol derivatives which are preferably phenol derivatives, more preferred resorcinol derivatives; in particular the active agents are preferably not carboxylic acid derivatives.

A further important aspect of the present invention is the use of the spray dried composition of the invention to reduce and/or inhibit stinging, pricking, tingling and burning sensations of cosmetic preparations which are applied to the skin.

Spray drying the stinging, pricking, tingling and burning active agents, the penetration through the skin, especially through the epidermis can be improved, thus smaller concentration of the described active agents can be used to achieved good efficacy, and simultaneously the stinging, pricking, tingling and burning of the skin caused by the active agents could be reduced, because the agent is encapsulated.

It has been recognized that the spray dried composition as described herein, can be formulated in different cosmetic preparations and formulations.

Thus, typical embodiments are creams, gels e.g. but not limited to hydrogels, hydrodispersion gels, oil gels; lotions, alcoholic and aqueous/alcoholic solutions, emulsions in their various forms for example but not limited to oil in water (O/W), water in oil (W/O), mixed emulsions, PIT emulsions, Pickering emulsions, micro-emulsions, nano-emulsions; aerosol foams, non-aerosol foams, aerosols sprays, non-aerosol sprays, pump sprays, serums, roll-ons, pastes, balsams, or stick preparations.

In a further embodiment of the invention the cosmetic preparation is preferably a skin whitening preparation, a leave-on hair product, a hair coloration.

It has been further shown that when formulating the spray dried composition as described herein into cosmetic preparations stable cosmetic formulations can be obtained without disadvantage influences to the cosmetic preparations regarding the stability of the formulations or the function of the stinging, pricking, tingling and burning active agents, e.g. for the whitening capacity of the whitening agent.

Thus, a further object of the invention is a cosmetic preparation comprising (i) a spay dried composition as defined herein, which comprises one or more active agents which causes discomfort feelings like stinging, pricking, tingling and burning sensation when applied onto skin, and one or more carrier materials which are selected from the group consisting of sugar, sugar derivatives, modified starch, triglycerides, fatty alcohols or esters of fatty alcohols and fatty acids, proteins, celluloses, salts, dextrins, gums, sugar alcohols, polyols, peptides, acids, carbohydrates, hydrocolloids or a mixture thereof, and (ii) a further cosmetically ingredients.

A further object of the invention is a skin care composition comprising at least one or more active agents which generate stinging, pricking, tingling and burning to human skin upon application thereto, wherein all of said active agents are preferably derivatives from an alcohol, particularly alcohol derivatives which are preferably phenol derivatives, more preferred resorcinol derivatives; in particular the active agents are preferably not carboxylic acid derivatives, are spray dried, wherein the carrier material is selected from the group consisting of sugar, sugar derivatives, modified starch, triglycerides, fatty alcohols or esters of fatty alcohols and fatty acids, proteins, celluloses, salts, dextrins, gums, sugar alcohols, polyols, peptides, acids, carbohydrates, hydrocolloids or a mixture thereof.

It has been shown that using the said spray dried composition in cosmetic preparations, especially skin care composition, with the combination of the stinging, pricking, tingling and burning active agents that are derivatives of alcohols and the specific carrier materials as defined herein a perceptible reduced skin stinging and improved skin feeling could be achieved.

In one preferred embodiment of the invention the spray dried composition of the present invention is to be formulated into a cosmetic preparation comprises spray dried whitening agents or brightening agents, wherein the whitening (or brightening) agent is preferably a skin whitening agent, preferably 4-(1-Phenylethyl) 1-,3 benzenediol. Such a composition may further comprise cis- and/or trans-4-tert-Butylcyclohexanol or solutions of trans-4-tert-Butylcyclohexanol as another preferred embodiment.

In a preferred embodiment of the present invention the cosmetic preparation of the present invention is, depending on their formulation, a dermatological preparation and can be used as skin cream as day cream or night cream, milk, lotion, deo and antiperspirant formulations. The preparation can also be used, depending on their formulation, in hair care compositions such as shampoos, hair coloration, hair tonics, hair lotions, hair rinses, sprays, etc.

In some instances, it is possible and advantageous to use the preparations according to the present invention as bases for pharmaceutical preparations. Preference is given, in particular, to those cosmetic or pharmaceutical and dermatological preparations in the form of a skin care, hair care or make-up product.

An important object of the present invention is the use of one or more carrier materials selected from the group consisting of sugar, sugar derivatives, modified starch, triglycerides, fatty alcohols or esters of fatty alcohols and fatty acids, proteins, celluloses, salts, dextrins, gums, sugar alcohols, polyols, peptides, acids, carbohydrates, hydrocolloids or a mixture thereof, in a spray dry process for producing a spray dried composition comprising one or more stinging, pricking, tingling and burning active agents. The use is preferably for reducing/inhibiting stinging, pricking, tingling and burning of the skin, when formulated these active agents into cosmetic preparations, especially topical cosmetic preparations, in particular for skin.

The carrier materials and stinging, pricking, tingling and burning active agents are as defined herein.

The term "skin" as used herein includes the skin on the face, neck, chest, back, arms, armpits, hands and scalp.

The terms "sting", "burn", "prick" and "ting" as used herein are synonymous and are used interchangeably.

Maltodextrin

Maltodextrin is available in various qualities. A preferred maltodextrin, suitable as carrier material in the sense of the present invention possess the following specification:

Dextrose 0.1-10%, preferably 1-5%, more preferably 2-3%;

Maltose 0.1-10%, preferably 2-9%, more preferably 5-7%;

Triose 0.1-15%, preferably 5-13%, more preferably 7-10%;

Higher Polysaccharides: 70-95%, preferably 70-90%, more preferably 75-82%

Modified Starch

A modified starch in the sense of the invention is a starch that has been chemically modified to allow the starch to function properly under conditions frequently encountered during processing or storage, such as high heat, high shear, low pH, freeze/thaw and cooling.

The modified food starches are E coded according to the International Numbering System for Food Additives (INS): [30]

1400 Dextrin
1401 Acid-treated starch
1402 Alkaline-treated starch
1403 Bleached starch
1404 Oxidized starch
1405 Starches, enzyme-treated
1410 Monostarch phosphate
1412 Distarch phosphate
1413 Phosphated distarch phosphate
1414 Acetylated distarch phosphate
1420 Starch acetate
1422 Acetylated distarch adipate
1440 Hydroxypropyl starch
1442 Hydroxypropyl distarch phosphate
1443 Hydroxypropyl distarch glycerol
1450 Starch sodium octenyl succinate
1451 Acetylated oxidized starch Suitable modified starch in the sense of the present invention preferably base on potato starch, wheat starch, rice starch and corn starch, and mixture thereof.

Resorcinol Derivatives

Resorcinol derivatives are well known compounds that can be obtained in the market. Preferably, the compounds are selected from the group consisting of butyl resorcinol, pentyl resorcinol, hexyl resorcinol, heptyl resorcinol, octyl resorcinol, nonyl resorcinol, decylresorcinol, phenylethyl resorcinol, phenylpropyl resorcinol, phenylbutyl resorcinol, phenylhexyl resorcinol, toluoylethyl resorcinol, toluoylpropyl resorcinol, toluoylbutyl resorcinol, toluoylhexyl resorcinol, methoxytoluoylethyl resorcinol, methoxytoluoylpropyl resorcinol, methoxytoluoylbutyl resorcinol, methoxyltoluoylhexyl resorcinol, dimethoxytoluoylethyl resorcinol, dimethoxytoluoylpropyl resorcinol, dimethoxytoluoylbutyl resorcinol, dimethoxytoluoylhexyl resorcinol and their mixtures. The preferred structures are hexyl resorcinol, dimethoxytoluoylhexyl resorcinol and in particular Phenylethyl resorcinol.

An overall preferred spray dried composition comprises
(i) at least 3-phenylethyl resorcinol as active agents, and
(ii) maltodextrin, especially as defined herein, as carrier material.

Cosmetic or Personal Care Composition

Another object of the present invention encompasses a cosmetic or personal care composition. The cosmetic or personal care composition may represent a skin care, hair care and/or sun care product, such as for example a cosmetic cream, lotion, spray, emulsion, ointment, gel or mouse and the like. Typical examples are skin creams and hair shampoos, antiperspirants and soaps.

The preparations according to the invention may contain abrasives, anti-acne agents, agents against ageing of the skin, anti-cellulitis agents, antidandruff agents, anti-inflammatory agents, irritation-preventing agents, irritation-inhibiting agents, antioxidants, astringents, perspiration-inhibiting agents, antiseptic agents, anti-statics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, hair promotion agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxyl acids, polyhydroxyfatty acids, liquefiers, dyestuffs, colour-protecting agents, pigments, anti-corrosives, aromas, flavouring substances, odoriferous substances, polyols, surfactants, electrolytes, organic solvents or silicone derivatives and the like as additional auxiliaries and additives.

Surfactants

Preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and di-alkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular dioctyl malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial Glycerides.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan Esters.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol Esters.

Typical examples of suitable polyglycerol esters are Polyglyceryl-2 Dipolyhydroxystea rate (Dehymuls® PGPH), Polyglycerin-3-Diisostea rate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic Emulsifiers.

Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric Emulsifiers.

Other suitable emulsifiers are amphoteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocomidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO₃H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, GrUnau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bisdimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlizing Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. In Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

The UV filters cited below which can be used within the context of the present invention are preferred but naturally are not limiting.

UV filters which are preferably used are selected from the group consisting of
p-aminobenzoic acid
p-aminobenzoic acid ethyl ester (25 mol) ethoxylated (INCI name: PEG-25 PABA)
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan® HMS)
salicylic acid-2-ethylhexyl ester (Neo Heliopan® OS)
triethanolamine salicylate
4-isopropyl benzyl salicylate
anthranilic acid menthyl ester (Neo Heliopan® MA)
diisopropyl cinnamic acid ethyl ester
p-methoxycinnamic acid-2-ethylhexyl ester (Neo Heliopan® AV)
diisopropyl cinnamic acid methyl ester
p-methoxycinnamic acid isoamyl ester (Neo Heliopan® E 1000)
p-methoxycinnamic acid diethanolamine salt
p-methoxycinnamic acid isopropyl ester
2-phenylbenzimidazole sulfonic acid and salts (Neo Heliopan® Hydro)
3-(4'-trimethylammonium) benzylidene bornan-2-one methyl sulfate
beta-imidazole-4(5)-acrylic acid (urocanic acid)
3-(4'-sulfo)benzylidene bornan-2-one and salts
3-(4'-methyl benzylidene)-D,L-camphor (Neo Heliopan® BC)
3-benzylidene-D,L-camphor
N-[(2 and 4)-[2-(oxoborn-3-ylidene) methyl]benzyl] acrylamide polymer
4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb® HEB)
benzylidene malonate polysiloxane (Parsol® SLX)
glyceryl ethylhexanoate dimethoxycinnamate
dipropylene glycol salicylate
tris(2-ethylhexyl)-4,4',4"-(1,3,5-triazine-2,4,6-triyltriimino) tribenzoate (=2,4,6-trianilino-(p-carbo-2'-ethylhexyl-1'-oxy)-1,3,5-triazine) (Uvinul® T150).

Broadband filters which are preferably used in preparation according to the present invention are selected from the group consisting of
2-ethylhexyl-2-cyano-3,3-diphenyl acrylate (Neo Heliopan® 303)
ethyl-2-cyano-3,3'-diphenyl acrylate
2-hydroxy-4-methoxybenzophenone (Neo Heliopan® BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
sodium hydroxymethoxybenzophenone sulfonate
disodium-2,2'-dihydroxy-4,4'-dimethoxy-5,5'-disulfobenzophenone
phenol, 2-(2H-benzotriazol-2-yl)-4-methyl-6-(2-methyl-3 (1,3,3,3-tetramethyl-1-(trimethylsilyl)oxy)disiloxyanyl) propyl) (Mexoryl® XL)
2,2'-methylene bis-(6-(2H-benzotriazol-2-yl)-4-1,1,3,3-tetramethylbutyl) phenol) (Tinosorb® M)
2,4-bis-[4-(2-ethylhexyloxy)-2-hydroxyphenyl]-1,3,5-triazine 2,4-bis-[{(4-(2-ethylhexyloxy)-2-hydroxy}phenyl]-6-(4-methoxyphenyl)-1,3,5-triazine (Tinosorb® S)
2,4-bis-[{(4-(3-sulfonato)-2-hydroxypropyloxy)-2-hydroxy}) phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethyl carbonyl) phenylamino]-1,3,5-triazine
2,4-bis-[{4-(3-(2-propyloxy)-2-hydroxypropyloxy)-2-hydroxy}) phenyl]-6-[4-(2-ethylcarboxyl) phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2"-methylpropenyloxy)-2-hydroxy}phenyl]-6-(4-methoxyphenyl)-1,3,5-triazine
2,4-bis-[{4-(1',1',1',3',5',5',5'-heptamethylsiloxy-2"-methylpropyloxy)-2-hydroxy}) phenyl]-6-(4-methoxyphenyl)-1,3,5-triazine.

The compositions can comprise further typical detergent and cleansing composition ingredients such as UV-A filters which are preferably selected from the group consisting of
4-isopropyl dibenzoyl methane
terephthalylidene dibornane sulfonic acid and salts (Mexoryl® SX)
4-t-butyl-4'-methoxydibenzoyl methane (avobenzone)/(Neo Heliopan® 357)
phenylene bis-benzimidazyl tetrasulfonic acid disodium salt (Neo Heliopan® AP)
2,2'-(1,4-phenylene)-bis-(1H-benzimidazole-4,6-disulfonic acid), monosodium salt
2-(4-diethylamino-2-hydroxybenzoyl) benzoic acid hexyl ester (Uvinul® A Plus)
indanylidene compounds in accordance with DE 100 55 940 A1 (=WO 2002 038537 A1)

The compositions can comprise further typical detergent and cleansing composition ingredients such as UV filters which are selected from the group consisting of
p-aminobenzoic acid
3-(4'-trimethylammonium) benzylidene bornan-2-one methyl sulfate
salicylic acid homomenthyl ester (Neo Heliopan® HMS)
2-hydroxy-4-methoxybenzophenone (Neo Heliopan® BB)
2-phenylbenzimidazole sulfonic acid (Neo Heliopan® Hydro)
terephthalylidene dibornane sulfonic acid and salts (Mexoryl® SX)
4-tert-butyl-4'-methoxydibenzoyl methane (Neo Heliopan® 357)
3-(4'-sulfo)benzylidene bornan-2-one and salts
2-ethylhexyl-2-cyano-3,3-diphenyl acrylate (Neo Heliopan® 303)
N-[(2 and 4)-[2-(oxoborn-3-ylidene) methyl]benzyl] acrylamide polymer
p-methoxycinnamic acid-2-ethylhexyl ester (Neo Heliopan® AV)
p-aminobenzoic acid ethyl ester (25 mol) ethoxylated (INCI name: PEG-25 PABA)
p-methoxycinnamic acid isoamyl ester (Neo Heliopan® E1000)
2,4,6-trianilino-(p-carbo-2'-ethylhexyl-1'-oxy)-1,3,5-triazine (Uvinul® T150)
phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl® XL)
4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb HEB)
3-(4'-methyl benzylidene)-D,L-camphor (Neo Heliopan® BC)
3-benzylidene camphor
salicylic acid-2-ethylhexyl ester (Neo Heliopan® OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl) phenol) (Tinosorb® M)
phenylene bis-benzimidazyl tetrasulfonic acid disodium salt (Neo Heliopan® AP)
2,4-bis-[{(4-(2-ethylhexyloxy)-2-hydroxy}phenyl]-6-(4-methoxyphenyl)-1,3,5-triazine (Tinosorb® S)
benzylidene malonate polysiloxane (Parsol® SLX)
menthyl anthranilate (Neo Heliopan® MA)
2-(4-diethylamino-2-hydroxybenzoyl) benzoic acid hexyl ester (Uvinul® A Plus)
indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine)

in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobic, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Actives Modulating Skin and/or Hair Pigmentation

Preferred active ingredients for skin and/or hair lightening are selected from the group consisting of: kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfurcontaining molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, papaya extract, turmeric extract, mulberry extract, bengkoang extract, nutgrass extract, liquorice root extract or constituents concentrated or isolated therefrom, preferably glabridin or licochalcone A, artocarpus extract, extract of rumex and ramulus species, extracts of pine species (pinus), extracts of vitis species or stilbene derivatives isolated or concentrated therefrom, saxifrage extract, scutelleria extract, grape extract and/or microalgae extract, in particular *Tetraselmis suecica* Extract.

Preferred skin lighteners as component (b) are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, papaya extract, turmeric extract, nutgrass extract, licorice extract (containing glycyrrhizin), alpha-hydroxy-acids, 4-alkylresorcinols, 4-hydroxyanisole. These skin lighteners are preferred due to their very good activity, in particular in combination with sclareolide according to the present invention. In addition, said preferred skin lighteners are readily available.

Advantageous skin and hair tanning active ingredients in this respect are substrates or substrate analogues of tyrosinase such as L-tyrosine, N-acetyl tyrosine, L-DOPA or Ldihydroxyphenylalanine, xanthine alkaloids such as caffeine, theobromine and theophylline and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocatalases") as described for example in EP 0 584 178, tetrasubstituted cyclohexene derivatives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and analogues thereof, activators of adenylate cyclase and compounds which activate the transfer of melanosomes to keratinocytes such as serine proteases or agonists of the PAR-2 receptor, extracts of plants and plant parts of the chrysanthemum species, sanguisorba species, walnut extracts, urucum extracts, rhubarb extracts, microalgae extracts, in particular *Isochrysis galbana*, trehalose, erythrulose and dihydroxyacetone. Flavonoids which bring about skin and hair tinting or browning (e.g. quercetin, rhamnetin, kaempferol, fisetin, genistein, daidzein, chrysin and apigenin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Anti-Ageing Actives

In the context of the invention, anti-ageing or biogenic agents are, for example antioxidants, matrix-metalloproteinase inhibitors (MMPI), skin moisturizing agents, glycosaminglycan stimulkators, anti-inflammatory agents, TRPV1 antagonists and plant extracts.

Antioxidants.

Suitable antioxidants encompass amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to µmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, ginseng, liquorice, honeysuckle, sophora, pueraria, pinus, citrus, Phyllanthus emblica or St. John's wort, grape seeds, wheat germ, Phyllanthus emblica, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

If vitamin E and/or derivatives thereof are used as the antioxidant(s), it is advantageous to choose their concentrations from the range from about 0.001 to about 10% b.w. based on the total weight of the formulation. If vitamin A or vitamin A derivatives or carotenes or derivatives thereof are used as the antioxidant(s), it is advantageous to choose their concentrations from the range from about 0.001 to about 10% b.w. based on the total weight of the formulation.

Matrix-Metalloproteinase Inhibitors (MMPI).

Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1(2H)-benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsufonylfluoride, collhibin (company Pentapharm; INCI: hydrolysed rice protein), oenotherol (company Soliance; INCI: propylene glycol, aqua, Oenothera biennis root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus edodes extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, Rubus fruticosus (Blackberry) Leaf Extract). Preferred actives of are selected from the group consisting of retinyl palmitate, ursolic acid, extracts from the leaves of the Rosaceae family, sub-family Rosoideae, genistein and daidzein.

Skin-Moisturizing Agents.

Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

Glycosamlnoglycan Stimulators.

Preferred compositions comprise substances stimulating the synthesis of glycosaminoglycans selected from the group consisting of hyaluronic acid and derivatives or salts, Subliskin (Sederma, INCI: Sinorhizobium meliloti Ferment Filtrate, Cetyl Hydroxyethylcellulose, Lecithin), Hyalufix (BASF, INCI: Water, Butylene Glycol, Alpinia galanga leaf extract, Xanthan Gum, Caprylic/Capric Triglyceride), Stimulhyal (Soliance, INCI: Calcium ketogluconate), Syn- Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, Eriobotrya japonica extract, Genkwanin, N-Methyl-Lserine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, Sinorhizobium *Meliloti* Ferment Filtrate, Calcium ketogluconate, Alpinia galanga leaf extract and tetradecyl aminobutyroylvalylaminobutyric urea trifluoroacetate.

Anti-Inflammatory Agents.

The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, *Commiphora* species, *Rubia* species, willow, willow-herb, oats, calendula, arnica, St John's wort, honeysuckle, rosemary, *Passiflora* incarnata, witch hazel, ginger or *Echinacea*; preferably selected from the group consisting of extracts or fractions from camomile, Aloe vera, oats, calendula, arnica, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occurring avenanthramides, preferably tranilast, avenanthramide A, avenanthramide B, avenanthramide C, non-natural or non-naturally occurring avenanthramides, preferably dihydroavenanthramide D, dihydroavenanthramide E, avenanthramide D, avenanthramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and 3-glucans, in particular 1,3-1,4-β-glucan from oats.

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of Vanillosmopsis (in particular Vanillosmopsis erythropappa or Vanillosmopsis arborea). Synthetic alpha-bisabolol is obtainable, for example, under the name "Dragosantol" from Symrise.

Trpv1 Antagonists.

Suitable compounds which reduce the hypersensitivity of skin nerves based on their action as TRPV1 antagonists encompass e.g. trans-4-tert-butyl cyclohexanol as described in WO 2009 087242 A1, or indirect modulators of TRPV1 by an activation of the g-receptor, e.g. acetyl tetrapeptide-15, are preferred.

Desquamating Agents.

The compositions may also contain desquamating agents (component b5) in amounts of about 0.1 to about 30% b.w. preferably about 0.5 to about 15% b.w., particularly preferably about 1 to about 10% b.w. based on the total weight of the preparation. The expression "desquamating agent" is understood to mean any compound capable of acting:

either directly on desquamation by promoting exfoliation, such as β-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of *Sophora japonica*; resveratrol and some derivatives of jasmonic acid;

or on the enzymes involved in the desquamation or the degradation of the corneodesmosomes, glycosidases, stratum corneum chymotryptic enzyme (SCCE) or other proteases (trypsin, chymotrypsin-like). There may be mentioned agents chelating inorganic salts: EDTA; N-acyl-N,N',N'-ethylenediaminetriacetic acid; aminosulphonic compounds and in particular (N-2-hydroxyethylpiperazine-N-2-ethane)sulphonic acid (HEPES); derivatives of 2-oxothiazolidine-4-carboxylic acid (procysteine); derivatives of alpha-amino acids of the glycine type (as described in EP-O 852 949, and sodium methylglycine diacetate marketed by BASF under the trade name TRILON M); honey; sugar derivatives such as O-octanoyl-6-D-maltose and Nacetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, a-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), 3-hydroxy acids such as salicylic acid and its derivatives, retinoids such as retinol and its esters, retinal, retinoic acid and its derivatives, those described in the documents FR 2570377 A1, EP 0199636 A1, EP 0325540 A1, EP 0402072 A1, chestnut or prickly pear extracts, in particular marketed by SILAB; reducing compounds such as cysteine or cysteine precursors.

Desquamating agents which can be used are also nicotinic acid and its esters and nicotinamide, also called vitamin B3 or vitamin PP, and ascorbic acid and its precursors, as described in particular in application EP 1529522 A1.

Anti-Cellulite Agents.

Anti-cellulite agents and lipolytic agents are preferably selected from the group consisting of those described in WO 2007/077541, and betaadrenergic receptor agonists such as synephrine and its derivatives, and cyclohexyl carbamates described in WO 2010/097479. Agents enhancing or boosting the activity of anti-cellulite agents, in particular agents which stimulate and/or depolarise C nerve fibres, are preferably selected from the group consisting of capsaicin and derivatives thereof, vanillylnonylamid and derivatives thereof, L-carnitine, coenzym A, isoflavonoides, soy extracts, ananas extract and conjugated linoleic acid.

Fat Enhancing Agents.

Formulations and products according to the present invention may also comprise one or more fat enhancing and/or adipogenic agents as well as agents enhancing or boosting the activity of fat enhancing agents. A fat enhancing agent is for example hydroxymethoxyphenyl propylmethylmethoxybenzofuran (trade name: Sym3D®).

Hair Growth Activators or Inhibitors

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-betacitronellol, panthenol, glycogen for example from mussels, extracts from microorganisms, algae, plants and plant parts of for example the genera dandelion (Leontodon or Taraxacum), *Orthosiphon, Vitex, Coffea, Paullinia, Theobroma, Asiasarum, Cucurbita* or *Styphnolobium, Serenoa repens* (saw palmetto), *Sophora flavescens, Pygeum africanum, Panicum miliaceum, Cimicifuga racemosa, Glycine max, Eugenia caryophyllata, Cotinus coggygria, Hibiscus rosa-sinensis, Camellia sinensis, Ilex paraguariensis, Isochrysis galbana*, licorice, grape, apple, barley or hops or/and hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gammaglutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* or *Gymnema sylvestre*.

Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (1-menthoxy)-2-methyl-1,2-propandiol, I-menthyl-methylether), menthylesters (for example menthylformiate, menthylacetate, menthylisobutyrate, menthyllactates, Lmenthyl-L-lactate, L-menthyl-D-lactate, menthyl-(2-methoxy)acetate, menthyl-(2-methoxyethoxy) acetate, menthylpyrogluta mate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, monomenthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or $N^{\alpha}$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (I-(−)isopulegol, I-(−)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-pmenthanecarboxamide or related compounds), (1R,2S,5R)—N-(4-Methoxyphenyl)-5-methyl-2-(1-isopropyl)cyclohexa ne-carboxamide [WS12], oxamates (preferably those described in EP 2033688 A2).

Anti-Microbial Agents

Suitable anti-microbial agents are, in principle, all substances effective against Grampositive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3, 5-dimethyl-phenol, 2,2'-methylenebis(6-bromo-4-chloro-phenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, 3-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxy-allantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 2 to 20, preferably of 10-20), lactose, silicon dioxide, dry glucose syrup with an dextrose equivalent value of 20-40, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;
alkylene glycols such as, for example, ethylene glycol, diethylene glycol, propylene glycol, butylene glycol, hexylene glycol and polyethylene glycols with an average molecular weight of 100 to 1000 Dalton;
technical oligoglycerol mixtures with a degree of self-condensation of 1.5 to 10, such as for example technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example methyl and butyl glucoside;
sugar alcohols containing 5 to 12 carbon atoms, for example sorbitol or mannitol,
sugars containing 5 to 12 carbon atoms, for example glucose or sucrose;
amino sugars, for example glucamine;
dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, and alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, ☐-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, laudanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemle, Welnhelm, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO (OH)) and/or tin oxide. Advantageous dyes are for example carmine, Berlin blue, chromium oxide green, ultramarine blue and/or manganese violet.

Preparations

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, crème, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, after sun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

EXAMPLES

Example 1

Preparation of Spray Dried Compositions A-E
Spray Drying Process

TABLE 1

Spray dried compositions A-E

| Formulation/Ingredients | A | B | C | D | E |
|---|---|---|---|---|---|
| Sodium starch octenylsuccinate | 30.0 | | | | |
| Glyceryl Oleat Citrate | | | | | 5.0 |
| Gummi Arabicum | | 25.0 | | | 20.0 |
| Calcium Caseinat | | | 5.0 | | |
| Inulin | | | Ad100 | | |
| Dextrin | | | | Ad100 | Ad100 |
| Trehalose | | Ad100 | | | |
| Maltodextrin | ad100 | | | 20.0 | |
| 4-(1-phenylethyl) 1-,3 benzenediol | 20.0 | 10.0 | | 20.0 | 20.0 |
| 4-Butylresorcinol | | | 15.0 | | |
| Caprylic/capric triglycerides | 20.0 | | | 10.0 | 15.0 |
| Ethylhexyl Isononanoate | | 15.0 | | 10.0 | |
| Pentylene Glycol, 4 Butylcyclohexanol | | | | | 2.0 |
| Pentylene Glycol | | 5.0 | | | |
| Soy Bean Oil | | | 10.0 | | |
| Butylene Glycol | | | 5.0 | | 5.0 |

Production Method:

Blend components with water and emulsify (ultra turrax stirrer) to a viscosity of 50-300 mPas, preferably to 150 mPas. Inlet temperature: 200° C. (+/−5° C.), outlet temperature: 90° C. (+/−5°).

Example 2

In Vivo Test Evaluation of Stinging Sensation of the Stinging, Pricking, Tingling and Burning Active Agents The test was performed with 38 trained panelists by pairwise comparison in the cheek area of the face after one single application. Sample amount of emulsion: 0.1 g. Formula 1 and formula 2 (single blinded) was simultaneously distributed onto the cheeks by 5× circulations with the fore-, and middle finger. Formula 1 (table 2) contains 0.5% 4-(1-Phenylethyl) 1-,3 benzenediol, formula 2 (table 2) contains 2.5% of spray dried active. (composition see table 1). Stinging sensation was evaluated after 5 minutes. Subjects were asked to identify whether there is a difference in skin feel and rate the formula with the lowest stinging sensation.

TABLE 2 o/w emulsion comprising spray dried composition A of example 1

| Phase | INCI | Formula 1 | Formula 2 |
|---|---|---|---|
| A. | Water(aqua) | 85.75 | 85.75 |
| | Glycerin | 2.5 | 2.5 |
| | Hydroxyacetophenone | 0.7 | 0.7 |
| | Disodium EDTA | 0.1 | 0.1 |
| B. | Ethylhexyl isononanoate | 3.0 | 3.0 |
| | Diisopropyl adipate | 1.0 | 1.0 |
| | Cetearyl ethylhexanoate | 3.0 | 3.0 |
| | Acrylates/C10-10 alkyl acrylate crosspolymer | 0.5 | 0.5 |
| C. | Sodium Hydroxide, 10% aquous sol. | 0.95 | 0.95 |
| D. | Spray dried composition A | — | 2.5 |
| | 4-(1-Phenylethyl) 1-,3 benzenediol | 0.5 | — |
| | Sum | 100.0 | 100.0 |

Production Method:

Heat Phase A and separately to approx. 80° C. Disperse Carbomer in phase B. Add B to A and homogenize for 2 min by using an ultra turrax stirrer. Add sodium hydroxide solution (Phase C) for neutralization while stirring. Add phase D to the finished formulation and stir for approx. 10 min.

Results:

A difference in skin feel could be detected by 76% of the subjects within formula 1+2. In a second question 66% of the subjects stated that formula 2 containing 2.5% of spray dried composition (=0.5% active 4-(1-Phenylethyl)-1,3-benzenediol) showed the lowest stinging sensation in comparison to formula 1 containing 0.5% of the non spray dried active 4-(1-Phenylethyl)-1,3-benzenediol.

Example 3

In Vivo Stinging Evaluation of Spray Dried Active Vs Components of Spray Dried Compositions The aim of this study was to evaluate whether the single components of the spray dried mixture (caprylic/capric/triglycerides, maltodextrin, sodium starch octenylsuccinate) may also reduce stinging sensation when added to the formula at the same dosage as in the spray dried product.

Formula A (table 3): 2.5% spray dried composition A (table 1)

Formula B (table 3): 0.5% 4-(1-Phenylethyl)-1,3-benzenediol
  0.5% Caprylic/Capric/Triglycerides
  0.75% Maltodextrin
  0.75% Sodium starch octenylsuccinate

TABLE 3 o/w emulsion

| Phase | INCI | Formula 2 | Formula 3 |
|---|---|---|---|
| A. | Water(aqua) | 85.75 | 85.75 |
|  | Glycerin | 2.5 | 2.5 |
|  | Hydroxyacetophenone | 0.7 | 0.7 |
|  | Disodium EDTA | 0.1 | 0.1 |
| B. | Ethylhexyl isononanoate | 3.0 | 3.0 |
|  | Diisopropyl adipate | 1.0 | 1.0 |
|  | Cetearyl ethylhexanoate | 3.0 | 3.0 |
|  | Acrylates/C10-10 alkyl acrylate crosspolymer | 0.5 | 0.5 |
| C. | Sodium hydroxide, 10% aquous sol. | 0.95 | 0.95 |
| D. | Spray dried composition A | 2.5 | — |
|  | Sodium starch octenylsuccinate | — | 0.75 |
|  | Maltodextrin | — | 0.75 |
|  | Phenylethyl resorcinol | — | 0.5 |
|  | Caprylic/capric triglycerides | — | 0.5 |
|  | Sum | 100.0 | 100.0 |
|  | pH value | 5.3 | 5.38 |

Production Method:

Heat Phase A and separately to approx. 80° C. Disperse Carbomer in phase B. Add B to A and homogenize for 2 min by using an ultra turrax stirrer. Add sodium hydroxide solution (Phase C) for neutralization while stirring. Add phase D to the finished formulation and stir for approx. 10 min.

Procedure:

The test was carried out with 11 volunteers using pairwise comparison in the cheek area of the face after one single application. Sample amount of emulsion: 0.1 g Formula 2 and 3 (single blinded) was simultaneously distributed onto the cheeks by 5× circulations with the fore-, and middle finger. Stinging sensation was evaluated after 5 minutes. Subjects were asked to identify whether there is a difference in skin feel and rate the formula with the lowest stinging sensation.

Results of In Vivo Study 2 (Table 3):

Eight out of eleven subjects identified that formula 2 containing 2.5% spray dried 4-(1-Phenylethyl) 1-,3 benzenediol (table 3) showed the lowest stinging sensation. Two subjects evaluated formula 3 containing the components in non-spray dried version as the lowest stinging formula. One subject could not find any difference in stinging sensation. In this test it could be significantly shown that the spray drying process leads to less stinging sensation in comparison to non-spray dried components.

Example 4

Formulation Examples I and II

In the following formulation examples are presented how to incorporate the mixtures according to the invention into cosmetic compositions. If not indicated otherwise, the different phases are prepared separately and then blended one after another.

TABLE 4

Formulation I: Hydrogel (amounts in % b.w.)

| Phase | INCI | Amount |
|---|---|---|
| A | Aqua | Ad 100 |
| B | Cetearyl Ethylhexanoate | 3.00 |
|  | Cetearyl Alcohol | 4.00 |
|  | Paraffinum Liquidum | 3.00 |
|  | Octyldodecanol | 4.00 |
|  | Dimethicone | 0.50 |
|  | Benzophenone-3 | 0.25 |
|  | Diethylhexyl Syringylidenemalonate, Caprylic/Capric Triglycerides | 0.30 |
| C | Acrylates/C10-30 Alkyl Acrylate Crosspolymer | 0.30 |
| D | Sodium Hydroxide, 10% sol | 0.68 |
| E | Aqua | 2.00 |
|  | Sodium Metabisulfite | 0.08 |
| F | Spray dried composition A (table 1) | 2.5 |

TABLE 5

Formulation II: BB Cream (amounts in % b.w.)

| Phase | INCI | Amount |
|---|---|---|
| A | Potassium Cetyl Phosphate, Hydrogenated Palm Glycerides | 2.00 |
|  | Triisononanoin | 2.50 |
|  | Ethylhexyl Isononanoate | 1.00 |
|  | Cetearyl Alcohol | 2.00 |
|  | Dimethicone | 1.00 |
|  | Pentylene Glycol, 4 Butylcyclohexanol | 1.5 |
|  | Cetearyl Nonanoate | 1.00 |
|  | Benzylidene Dimethoxydimethylin danone | 0.20 |
|  | Ethylhexyl Salicylate | 2.00 |
|  | Homosalate | 1.00 |
|  | Butyl Methoxydibenzoylmethane | 1.00 |
|  | Sodium Stearoyl Glutamate | 0.20 |
|  | Tocopheryl Acetate | 0.10 |
|  | Disodium EDTA | 0.10 |
| B | Xanthan Gum | 0.30 |
|  | Acrylates/C10-30 Alkyl Acrylate Crosspolymer | 0.15 |
|  | Polyethylene | 0.70 |

TABLE 5-continued

| Phase | INCI | Amount |
|---|---|---|
| | Formulation II: BB Cream (amounts in % b.w.) | |
| C | Aqua | Ad 100 |
| | Glycerin | 3.00 |
| | Phenoxyethanol, Decylene Glycol, 1,2-Hexandiol | 0.80 |
| D | Titanium Dioxide (and) Iron Oxides | 1.00 |
| | Iron Oxides | 0.05 |
| | Titanium Dioxide | 0.15 |
| E | Carnosin | 0.10 |
| | Water, Pentylene Glycol, Glycerin, Fructose, Urea, Citric Acid, Sodium Hydroxide, Maltose, Sodium PCA, Sodium Chloride, Sodium Lactate, Trehalose, Allantoin, Sodium Hyaluronate, Glucose | |
| | Diethylhexyl Syringylidenemalonate, Caprylic/Capric Triglycerides | 0.10 |
| | Propylene Glycol, water, *Prunus Avium* Wood Extract | 0.2 |
| F | Spray dried composition A (table 1) | 2.5 |

It has been shown that in case of the formulation I and II, when the active agent 4-(1-Phenylethyl) 1-,3 benzenediol is spray dried in accordance to the present invention less stinging, pricking, tingling and burning has been occurred than the same formulation I and II wherein the active agent is not spray dried as described herein.

Stability Test

The formulation A of example 1 has been formulated into a standard o/w formulation and the stability of the formulation has been shown to be stable at 5° C., 20° C. (RT) and 40° C. for 6 months. The formulations have been stored at 5° C., 20° C. (RT) and 40° C. for 6 months.

Further Formulation Examples F1 to F12

Formulations (compositions) comprising spray dried compositions A-E (table 1):

F1. Skin lightening day cream o/w
F2: Body lotion
F3: After sun balm
F4: Calming body spray
F5: Sunscreen lotion (o/w, broadband protection)
F6: w/o night cream
F7: Barrier repair cream
F8: Antiperspirant/deodorant roll-on
F9: Emulsion with UV-A/B-broadband protection
F10: Sun spray with UV-A/B-broadband protection with low oil content
F11: Skin-lightening balm with UV-A/UV-B protection
F12: Hair conditioner, leave on

| EAW MATERIAL/INCI | F1 | F2 | F3 | F4 | F5 | F6 | F7 | F8 | F9 | F10 | F11 | F12 |
|---|---|---|---|---|---|---|---|---|---|---|---|---|
| Spray Dried Composition A | 1.5 | 2.5 | | | | | 2.5 | | | 1.0 | 2.0 | 2.5 |
| Spray dried composition B | | | | 2.5 | | | | | | | | |
| Spray dried composition C | | | 5.0 | | | | | | | | | |
| Spray dried composition D | | | | | 2.0 | 3.0 | | | | | | |
| Spray dried composition D | | | | | | | | | 2.0 | 1.0 | | |
| 1.2-Hexanediol. Caprylylglycol. | | | | | | | | | | 0.5 | | |
| 1.2-Hexanediol. Caprylylglycol. Tropolone | 0.5 | | | | | | | | | | | |
| 4-Methylbenzyl-idene Camphor | | | | | 1.5 | | | | | 33.3 | 10.0 | |
| Acrylates/C10-30 Alkyl Acrylate Crosspolymer | | | 0.3 | 0.2 | | | | | | | | |
| Allantoin | | 0.2 | 0.1 | | | | 0.25 | | | | | |
| Aluminium Stearate | | | | | | 1.0 | | | | | | |
| Aluminium Zirconium Pentachloro-hydrate (40% aqueous solution) | | | | | | | | 37.0 | | | | |
| BHT | | | | | | 0.1 | | | | | | |
| Bisabolol | 0.3 | | | 0.1 | 0.3 | 0.2 | | | 0.1 | 0.1 | | |
| Bisabolol. *Zingiber Officinale* (Ginger) Root Extract | | | | 0.1 | | | | | | | | |
| Butyl Methoxy-dibenzoyl-methane | | | | | 1.0 | | | | | | | |
| Butylene Glycol | | | 5.0 | | | | | | | 3.0 | 3.0 | |

-continued

| RAW MATERIAL/INCI | % BY WEIGHT/FORMULATION EXAMPLE | | | | | | | | | | | |
|---|---|---|---|---|---|---|---|---|---|---|---|---|
| | F1 | F2 | F3 | F4 | F5 | F6 | F7 | F8 | F9 | F10 | F11 | F12 |
| *Butyrospermum Parkii* (Shea Butter) | | | 1.0 | | | | | | | | | |
| C12-15 Alkyl Benzoate | | | 5.0 | | 5.0 | | | | | | | |
| Caprylic/Capric Triglyceride | 6.0 | | | 4.0 | 2.0 | | 10.0 | | 2.0 | | | 1.0 |
| Carbomer | | 0.1 | | | 0.2 | | | | 0.2 | | | |
| Cetearyl Alcohol | | 3.0 | | | 1.0 | 12.0 | 2.0 | | | | | |
| Cetearyl Ethylhexoate | 3.0 | 5.0 | | 7.0 | | 12.0 | | | 3.0 | | 0.6 | 0.3 |
| Cetearyl Nonanoate | | | | | | | | | 1.5 | | | |
| Cetrimonium Chloride | | | | | | | | | | | | 0.5 |
| Cetyl Alcohol | 1.0 | | | | | | | | 1.2 | | | |
| Cetylhydroxyproline Palmitamide | | 0.1 | | | | | 0.5 | | | | | |
| Citric Acid | | 0.4 | | | | | | | 0.3 | | | |
| Climbazole | | | | | | | | | | | | |
| Cocamidopropyl Betaine | | | | | | | | | | 1.0 | 1.0 | |
| *Curcuma Longa* (Turmeric) Root Extract | | 1.5 | | | | | | | | | | |
| *Curcuma Xanthorrhiza* Root Extract | | | | | | | | 0.5 | | | | |
| *Curcuma Zedoaria* Leaf Extract | 2.0 | | 1.5 | | | | | | | | | |
| Cyclohexasiloxane and Cyclopentasiloxane | | | | | 2.0 | | | | | | | |
| Cyclomethicone | | | | 0.5 | | | | | | | | |
| Dicaprylyl Ether | | | 4.0 | | | | | | | | | |
| Diisopropyl Adipate | | | | | | | | | | 1.0 | 1.0 | |
| Dimethyl Phenylbutanol | | | | 0.5 | | | | | | | | |
| Disodium EDTA | | | | | 0.1 | | | | 0.1 | | | |
| Disodium Phenyl Dibenzimidazole Tetrasulfonate | | | | | 10 | | | | 22.0 | | 1.5 | |
| Ethanol | | | | | | | | 30.0 | | 13.0 | 5.0 | |
| Ethylhexyl Ethylisononanoate | | | | | | | 2.0 | | | | 0.1 | |
| Ethylhexyl Methoxycinnamate | 5.0 | | | | 3.0 | | | | | 25.0 | | |
| Ethylhexyl Salicylate | | | | | 5.0 | | | | | | 2.0 | |
| Farnesol | | | | | | | | 0.5 | | | | |
| Fragrance | | | | | | | | | 0.3 | | | |
| Fragrance | 0.3 | 0.3 | 0.3 | 0.2 | 0.4 | 0.4 | 0.3 | 1.0 | | 0.5 | 0.4 | 0.1 |
| Galactoarabinan | | | 0.3 | | | | | | | | | 1.5 |
| Glycerin | 3.0 | 2.0 | 4.0 | | 4.7 | 2.0 | 3.0 | | | | | |
| Glycerin. *Triticum Vulgare* (Wheat) Protein. Water (Aqua) | 1.0 | | | | | | | | | | | |
| Glycerin. Water (Aqua). *Camellia Sinensis* Leaf Extract | | 0.2 | | | | | | | | | | |
| Glycerin. Water (Aqua). *Rosmarinus officinalis* (Rosemary) Leaf Extract | | 0.3 | | | | | 0.5 | | | | | |
| Glyceryl Oleate Citrate. Caprylic/Capric Triglyceride | | | | 2.0 | | | | | | | | |
| Glyceryl Stearate | | 2.0 | | | | | 2.0 | | | 2.0 | 4.0 | |
| Glyceryl Stearate Citrate | 4.0 | | | | | | 1.5 | | | | | 1.0 |
| *Helianthus Annuus* (Sunflower) Seed Oil | | | | | 5.0 | | | | | | | |
| Hexyldecanol. Bisabolol. Cetylhydroxyproline Palmitamide. Stearic Acid. *Brassica Campestris* (Rapeseed) Sterols | | | | | | | 2.0 | | | | | |
| Homosalate | | | | | | | | | | 5.0 | 5.0 | |
| Hydroxyethyl-cellulose | | | | | | | 0.3 | | | | | |
| Isoamyl p-Methoxycinnamate | | | | | | | | | | | 5.0 | |

-continued

| EAW MATERIAL/INCI | F1 | F2 | F3 | F4 | F5 | F6 | F7 | F8 | F9 | F10 | F11 | F12 |
|---|---|---|---|---|---|---|---|---|---|---|---|---|
| Isopropyl Palmitate | 4.0 | | | | | | | | | | | |
| Kojic Acid | 1.0 | | | | | | | | 0.5 | 0.2 | 0.3 | |
| Laureth-9 | | | 0.5 | | | | | | | | | |
| Magnesium Chloride | | | | | | 0.7 | | | | | | |
| Maltodextrin. Rubus Fruticosus (Blackberry) Leaf Extract | | 0.1 | | | 0.3 | 1.0 | | | | | | |
| Menthone Glycerol Acetal | 0.5 | | | | 0.3 | | | | | | | |
| Menthyl Ethylamido Oxalate | | | | | | | | | 1.0 | | | |
| Menthyl Lactate | | | 0.8 | | | | | 0.2 | | | | |
| Mineral Oil | | | | 4.0 | | | | | | | | |
| Panthenol | | | 1.0 | | | | | | | | | |
| PEG-40 Hydrogenated Castor Oil. Trideceth-9. Water (Aqua) | | | | | | | | | 2.0 | | 2.2 | |
| Pentylene Glycol | | | | 5.0 | | | | | | | | |
| Pentylene Glycol. 4-t-Butylcyclohexanol | | 1.5 | | | | | | | 0.5 | | | |
| Pentylene Glycol. Butylene Glycol. Hydroxyphenyl Propamidobenzoic Acid | | 1.0 | | | | | 1.0 | | | | | |
| Phenoxyethanol. Decylene Glycol. 1.2 Hexanediol | | | | | | | | | | | | 0.5 |
| Phenylbenz-imidazole Sulfonic Acid | | | | | 6.7 | | | | | | | |
| Phenylethyl Resorcinol | 0.5 | | | | | | | | 0.5 | | 1.0 | |
| Polyacrylamide. C13-14 Isoparaffin. Laureth-7 | | | | | | | | | | | | |
| Polyglyceryl 3-Caprate | | | | | | | 0.3 | | | | | |
| Polyquaternium-10 | | | | | | | | | | | | 0.1 |
| Potassium Cetyl Phosphate. Hydrogenated Palm Glycerides | | 2.0 | | | 1.5 | | 2.0 | | 1.5 | | 0.1 | |
| Propylene Glycol | | 5.0 | | | | | | | | 0.8 | 0.8 | 0.8 |
| Propylene Glycol. Hamamelis Virginiana (Witch Hazel) Water. Water (Aqua). Hamamelis Virginiana (Witch Hazel) Extract | | | | | | 1.0 | | | | | | |
| Prunus dulcis | | | | | | 5.0 | | | | | | |
| Quaternium-52 | | | | | | | | | | | | 4.0 |
| Retinyl Palmitate | | | | | | 0.2 | | | | | | |
| Sodium Ascorbyl Phosphate | 2.0 | | 1.0 | | | | | | | | | |
| Sodium Cetearyl Sulfate | | | | | | | | | 0.7 | | | |
| Sodium Hydroxide | | | | | | | 0.3 | | | | | |
| Sodium Hydroxide | | | 0.3 | 0.6 | 0.4 | | | | 2.8 | | | |
| Sodium Laureth Sulfate | | | | | | | | | | | 4.0 | |
| Sorbitan Isostearate. Hydrogenated Castor Oil. Ceresin. Beeswax (Cera Alba) | | | | | | 6.0 | | | | | | |
| Sorbitol | | | | | | 2.0 | | | | | | |
| Stearyl Heptanoate. Stearyl Caprylate | | 2.0 | | | | | | | | | | |
| Tocopheryl Acetate | | | 0.5 | | 0.5 | 3.0 | 0.3 | | 0.5 | | | |
| Triclosan | | | | | | | | 0.3 | | | | |
| Trideceth-9. PEG-5 Ethylhexanoate. Water | | | | | | | | | | | | |

-continued

| EAW MATERIAL/INCI | \% BY WEIGHT/FORMULATION EXAMPLE ||||||||||||
| --- | --- | --- | --- | --- | --- | --- | --- | --- | --- | --- | --- | --- |
|  | F1 | F2 | F3 | F4 | F5 | F6 | F7 | F8 | F9 | F10 | F11 | F12 |
| Triethanolamine |  |  |  |  | 0.5 |  |  |  |  |  | 0.5 |  |
| Triisononanoin |  | 2.0 |  |  |  |  | 3.0 |  |  |  | 1.0 |  |
| Water (Aqua) |  |  |  |  |  |  | ad 100 |  |  |  |  |  |

The invention claimed is:

1. A composition consisting of
(i) at least one active agent selected from the group consisting of butyl resorcinol, pentyl resorcinol, hexyl resorcinol, heptyl resorcinol, octyl resorcinol, nonyl resorcinol, decylresorcinol, phenylethyl resorcinol, phenylpropyl resorcinol, phenylbutyl resorcinol, phenylhexyl resorcinol, toluoylethyl resorcinol, toluoylpropyl resorcinol, toluoylbutyl resorcinol, toluoylhexyl resorcinol, methoxytoluoylethyl resorcinol, methoxytoluoylpropyl resorcinol, methoxytoluoylbutyl resorcinol, methoxyltoluoylhexyl resorcinol, dimethoxytoluoylethyl resorcinol, dimethoxytoluoylpropyl resorcinol, dimethoxytoluoylbutyl resorcinol, dimethoxytoluoylhexyl resorcinol and mixtures thereof, and
(ii) a carrier which is a mixture of modified starch, maltodextrin, and capric/caprylic triglyceride, wherein components (i) and (ii) are jointly subjected to a spray-drying process.

2. The composition of claim 1, wherein the at least one active agent (i) is phenylethyl resorcinol.

3. The spray dried composition of claim 1, wherein the modified starch is sodium octenyl succinate starch.

4. A method of reducing and/or inhibiting stinging, pricking, tingling and burning sensation of a cosmetic preparation, comprising the following steps:
(A) providing the spray-dried composition of claim 1, and subsequently
(B) formulating the spray-dried product of step (A) into the cosmetic preparation, and
(C) applying said cosmetic formulation to human skin.

* * * * *